United States Patent
Harper et al.

(10) Patent No.: US 11,391,723 B2
(45) Date of Patent: *Jul. 19, 2022

(54) ANALYTE MONITORING SYSTEM AND METHODS OF USE

(71) Applicant: ABBOTT DIABETES CARE INC., Alameda, CA (US)

(72) Inventors: Wesley Scott Harper, Alameda, CA (US); Erwin Satrya Budiman, Fremont, CA (US); Kenneth J. Doniger, Menlo Park, CA (US); Gary Alan Hayter, Oakland, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 16/111,099

(22) Filed: Aug. 23, 2018

(65) Prior Publication Data
US 2018/0364215 A1    Dec. 20, 2018

Related U.S. Application Data

(63) Continuation of application No. 15/143,413, filed on Apr. 29, 2016, now Pat. No. 10,082,493, which is a
(Continued)

(51) Int. Cl.
*A61B 5/00* (2006.01)
*G01N 33/487* (2006.01)
(Continued)

(52) U.S. Cl.
CPC ..... *G01N 33/48792* (2013.01); *A61B 5/0004* (2013.01); *A61B 5/0026* (2013.01);
(Continued)

(58) Field of Classification Search
None
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| (Continued) | | |

FOREIGN PATENT DOCUMENTS

| | | |
|---|---|---|
| CA | 2468577 | 6/2003 |
| CA | 2678336 | 5/2008 |
| (Continued) | | |

OTHER PUBLICATIONS

Hovorka, R., et al., "Nonlinear Model Predictive Control of Glucose Concentration in Subjects with Type 1 Diabetes", *Physiological Measurement*, vol. 55, Jul. 2004, pp. 905-920.
(Continued)

*Primary Examiner* — Etsub D Berhanu
(74) *Attorney, Agent, or Firm* — Baker Botts L.L.P.

(57) ABSTRACT

The present disclosure provides methods of processing data provided by a transcutaneous or subcutaneous analyte sensor utilizing different algorithms to strike a balance between signal responsiveness accompanied by signal noise and the introduction of error associated with that noise. The methods utilize the strengths of a lag correction algorithm and a smoothing algorithm to optimize the quality and value of the resulting data (glucose concentrations and the rates of change in glucose concentrations) to a continuous glucose monitoring system. Also provided are systems and kits.

17 Claims, 6 Drawing Sheets

Related U.S. Application Data continuation of application No. 13/683,996, filed on Nov. 21, 2012, now Pat. No. 9,339,217.

(60) Provisional application No. 61/563,743, filed on Nov. 25, 2011.

(51) Int. Cl.
| | |
|---|---|
| *A61B 5/145* | (2006.01) |
| *A61M 5/172* | (2006.01) |
| *G16Z 99/00* | (2019.01) |
| *G01N 33/49* | (2006.01) |

(52) U.S. Cl.
CPC ........ *A61B 5/1451* (2013.01); *A61B 5/14503* (2013.01); *A61B 5/14532* (2013.01); *A61B 5/4839* (2013.01); *A61B 5/6833* (2013.01); *A61B 5/7225* (2013.01); *A61B 5/7275* (2013.01); *A61M 5/1723* (2013.01); *G01N 33/49* (2013.01); *G16Z 99/00* (2019.02); *A61B 5/002* (2013.01)

(56) References Cited

U.S. PATENT DOCUMENTS

| | | | |
|---|---|---|---|
| 3,949,388 A | 4/1976 | Fuller | |
| 3,960,497 A | 6/1976 | Acord et al. | |
| 4,033,330 A | 7/1977 | Willis et al. | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,392,849 A | 7/1983 | Petre et al. | |
| 4,425,920 A | 1/1984 | Bourland et al. | |
| 4,441,968 A | 4/1984 | Emmer et al. | |
| 4,462,048 A | 7/1984 | Ross | |
| 4,464,170 A | 8/1984 | Clemens et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |
| 4,671,288 A | 6/1987 | Gough | |
| 4,703,756 A | 11/1987 | Gough et al. | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |
| 4,779,618 A | 10/1988 | Mund et al. | |
| 4,847,785 A | 7/1989 | Stephens | |
| 4,854,322 A | 8/1989 | Ash et al. | |
| 4,871,351 A | 10/1989 | Feingold | |
| 4,890,620 A | 1/1990 | Gough | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,051,688 A | 9/1991 | Murase et al. | |
| 5,055,171 A | 10/1991 | Peck | |
| 5,068,536 A | 11/1991 | Rosenthal | |
| 5,077,476 A | 12/1991 | Rosenthal | |
| 5,082,550 A | 1/1992 | Rishpon et al. | |
| 5,106,365 A | 4/1992 | Hernandez | |
| 5,122,925 A | 6/1992 | Inpyn | |
| 5,135,004 A | 8/1992 | Adams et al. | |
| 5,165,407 A | 11/1992 | Wilson et al. | |
| 5,202,261 A | 4/1993 | Musho et al. | |
| 5,204,264 A | 4/1993 | Kaminer et al. | |
| 5,210,778 A | 5/1993 | Massart | |
| 5,228,449 A | 7/1993 | Christ et al. | |
| 5,231,988 A | 8/1993 | Wernicke et al. | |
| 5,246,867 A | 9/1993 | Lakowicz et al. | |
| 5,251,126 A | 10/1993 | Kahn et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,328,460 A | 7/1994 | Lord et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,384,547 A | 1/1995 | Lynk et al. | |
| 5,390,671 A | 2/1995 | Lord et al. | |
| 5,391,250 A | 2/1995 | Cheney, II et al. | |
| 5,408,999 A | 4/1995 | Singh et al. | |
| 5,410,326 A | 4/1995 | Goldstein | |
| 5,411,647 A | 5/1995 | Johnson et al. | |
| 5,425,868 A | 6/1995 | Pedersen | |
| 5,429,602 A | 7/1995 | Hauser | |
| 5,431,160 A | 7/1995 | Wilkins | |
| 5,431,921 A | 7/1995 | Thombre | |
| 5,438,983 A | 8/1995 | Falcone | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,552,997 A | 9/1996 | Massart | |
| 5,555,190 A | 9/1996 | Derby et al. | |
| 5,564,434 A | 10/1996 | Halperin et al. | |
| 5,568,400 A | 10/1996 | Stark et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,653,239 A | 8/1997 | Pompei et al. | |
| 5,660,163 A | 8/1997 | Schulman et al. | |
| 5,665,222 A | 9/1997 | Heller et al. | |
| 5,711,001 A | 1/1998 | Bussan et al. | |
| 5,711,861 A | 1/1998 | Ward et al. | |
| 5,726,646 A | 3/1998 | Bane et al. | |
| 5,733,259 A | 3/1998 | Valcke et al. | |
| 5,735,285 A | 4/1998 | Albert et al. | |
| 5,748,103 A | 5/1998 | Flach et al. | |
| 5,772,586 A | 6/1998 | Heinonen et al. | |
| 5,791,344 A | 8/1998 | Schulman et al. | |
| 5,899,855 A | 5/1999 | Brown | |
| 5,914,026 A | 6/1999 | Blubaugh, Jr. et al. | |
| 5,919,141 A | 7/1999 | Money et al. | |
| 5,925,021 A | 7/1999 | Castellano et al. | |
| 5,935,224 A | 8/1999 | Svancarek et al. | |
| 5,942,979 A | 8/1999 | Luppino | |
| 5,957,854 A | 9/1999 | Besson et al. | |
| 5,961,451 A | 10/1999 | Reber et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |

(56) References Cited

U.S. PATENT DOCUMENTS

| | | |
|---|---|---|
| 6,024,699 A | 2/2000 | Surwit et al. |
| 6,028,413 A | 2/2000 | Brockmann |
| 6,032,119 A | 2/2000 | Brown et al. |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,498,043 B1 | 12/2002 | Schulman et al. |
| 6,514,718 B2 | 2/2003 | Heller et al. |
| 6,544,212 B2 | 4/2003 | Galley et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,025 B1 | 5/2004 | Platt |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,015,817 B2 | 3/2006 | Copley et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,046,153 B2 | 5/2006 | Oja et al. |
| 7,052,483 B2 | 5/2006 | Wojcik |

(56) References Cited

U.S. PATENT DOCUMENTS

| | | |
|---|---|---|
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,241,266 B2 | 7/2007 | Zhou et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,401,111 B1 | 7/2008 | Batman et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,766,829 B2 | 8/2010 | Sloan et al. |
| 7,768,387 B2 | 8/2010 | Fennell et al. |
| 7,774,145 B2 | 8/2010 | Bruaker et al. |
| 7,778,680 B2 | 8/2010 | Goode, Jr. et al. |
| 7,785,256 B1 | 8/2010 | Koh |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode et al. |
| 7,885,698 B2 | 2/2011 | Feldman et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,976,467 B2 | 7/2011 | Young et al. |
| 7,978,063 B2 | 7/2011 | Baldus et al. |
| 7,996,158 B2 | 8/2011 | Hayter et al. |
| 8,005,524 B2 | 8/2011 | Brauker et al. |
| 8,010,174 B2 | 8/2011 | Goode et al. |
| 8,010,256 B2 | 8/2011 | Oowada |
| 8,066,639 B2 | 11/2011 | Nelson et al. |
| 8,160,900 B2 | 4/2012 | Taub et al. |
| 8,192,394 B2 | 6/2012 | Estes et al. |
| 8,207,859 B2 | 6/2012 | Enegren et al. |
| 8,216,138 B1 | 7/2012 | McGarraugh et al. |
| 8,255,026 B1 | 8/2012 | Al-Ali |
| 8,282,549 B2 | 10/2012 | Brauker et al. |
| 8,374,668 B1 | 2/2013 | Hayter et al. |
| 8,461,985 B2 | 6/2013 | Fennell et al. |
| 8,478,557 B2 | 7/2013 | Hayter et al. |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,710,993 B2 | 4/2014 | Hayter et al. |
| 8,730,058 B2 | 5/2014 | Harper |
| 8,834,366 B2 | 9/2014 | Hayter et al. |
| 8,845,536 B2 | 9/2014 | Brauker et al. |
| 9,289,179 B2 | 3/2016 | Hayter et al. |
| 2001/0037366 A1 | 11/2001 | Webb et al. |
| 2002/0019022 A1* | 2/2002 | Dunn ............... A61B 5/14532 435/14 |
| 2002/0042090 A1 | 4/2002 | Heller et al. |
| 2002/0054320 A1 | 5/2002 | Ogino |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1* | 7/2003 | Fox ............... A61B 5/14532 600/347 |
| 2003/0130616 A1 | 7/2003 | Steil et al. |
| 2003/0134347 A1 | 7/2003 | Heller et al. |

(56) References Cited

U.S. PATENT DOCUMENTS

| | | |
|---|---|---|
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |

(56) References Cited

U.S. PATENT DOCUMENTS

| | | |
|---|---|---|
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0290496 A1 | 12/2006 | Peeters et al. |
| 2006/0293607 A1 | 12/2006 | Alt et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0038053 A1 | 2/2007 | Berner et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0197889 A1 | 8/2007 | Brauker et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0255348 A1 | 11/2007 | Holtzclaw |
| 2007/0270672 A1 | 11/2007 | Hayter et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0234992 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saudara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278331 A1 | 11/2008 | Hayter et al. |
| 2008/0287755 A1 | 11/2008 | Sass et al. |
| 2008/0287761 A1* | 11/2008 | Hayter ............... G16H 40/40 600/365 |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |

(56) References Cited

U.S. PATENT DOCUMENTS

| | | |
|---|---|---|
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev |
| 2008/0319085 A1 | 12/2008 | Wright et al. |
| 2008/0319279 A1 | 12/2008 | Ramsay et al. |
| 2009/0005665 A1 | 1/2009 | Hayter et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054750 A1 | 2/2009 | Jennewine |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0093687 A1 | 4/2009 | Telfort et al. |
| 2009/0099436 A1 | 4/2009 | Brister et al. |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112154 A1 | 4/2009 | Montgomery et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1* | 8/2009 | Hayter ................ A61B 5/7221 600/347 |
| 2009/0203981 A1 | 8/2009 | Brauker et al. |
| 2009/0204341 A1 | 8/2009 | Brauker et al. |
| 2009/0210249 A1 | 8/2009 | Rasch-Menges et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0287073 A1 | 11/2009 | Boock et al. |
| 2009/0287074 A1 | 11/2009 | Shults et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0023291 A1 | 1/2010 | Hayter et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0093786 A1 | 4/2010 | Watanabe et al. |
| 2010/0094251 A1 | 4/2010 | Estes et al. |
| 2010/0095229 A1 | 4/2010 | Dixon et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |

(56) References Cited

U.S. PATENT DOCUMENTS

| | | |
|---|---|---|
| 2010/0152548 A1 | 6/2010 | Koski |
| 2010/0152554 A1 | 6/2010 | Steine et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0185175 A1 | 7/2010 | Kamen et al. |
| 2010/0191082 A1 | 7/2010 | Brister et al. |
| 2010/0191085 A1* | 7/2010 | Budiman ............ A61B 5/1495 600/365 |
| 2010/0191087 A1 | 7/2010 | Talbot et al. |
| 2010/0191472 A1 | 7/2010 | Doniger et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0212583 A1 | 8/2010 | Brister et al. |
| 2010/0213080 A1 | 8/2010 | Celentano et al. |
| 2010/0214104 A1 | 8/2010 | Goode et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0240976 A1 | 9/2010 | Goode et al. |
| 2010/0249530 A1 | 9/2010 | Rankers et al. |
| 2010/0259543 A1 | 10/2010 | Tarassenko et al. |
| 2010/0261987 A1 | 10/2010 | Kamath et al. |
| 2010/0265073 A1 | 10/2010 | Harper et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0277342 A1 | 11/2010 | Sicurello et al. |
| 2010/0280341 A1 | 11/2010 | Boock et al. |
| 2010/0280782 A1 | 11/2010 | Harper et al. |
| 2010/0286496 A1 | 11/2010 | Simpson et al. |
| 2010/0298684 A1 | 11/2010 | Leach et al. |
| 2010/0305965 A1 | 12/2010 | Benjamin et al. |
| 2010/0313105 A1 | 12/2010 | Nekoomaram et al. |
| 2010/0324403 A1 | 12/2010 | Brister et al. |
| 2010/0331644 A1 | 12/2010 | Neale et al. |
| 2010/0331648 A1 | 12/2010 | Kamath et al. |
| 2010/0331651 A1 | 12/2010 | Groll |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009724 A1 | 1/2011 | Hill et al. |
| 2011/0009727 A1 | 1/2011 | Mensinger et al. |
| 2011/0009813 A1 | 1/2011 | Rankers et al. |
| 2011/0010257 A1 | 1/2011 | Hill et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0046467 A1 | 2/2011 | Simpson et al. |
| 2011/0053121 A1 | 3/2011 | Heaton |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0105873 A1 | 5/2011 | Feldman et al. |
| 2011/0112696 A1 | 5/2011 | Yodfat et al. |
| 2011/0118579 A1 | 5/2011 | Goode et al. |
| 2011/0118580 A1 | 5/2011 | Goode et al. |
| 2011/0123971 A1 | 5/2011 | Berkowitz et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0126188 A1 | 5/2011 | Bernstein et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0163880 A1 | 7/2011 | Halff et al. |
| 2011/0163881 A1 | 7/2011 | Halff et al. |
| 2011/0178378 A1 | 7/2011 | Brister et al. |
| 2011/0184268 A1 | 7/2011 | Taub |
| 2011/0184752 A1 | 7/2011 | Ray et al. |
| 2011/0190614 A1 | 8/2011 | Brister et al. |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0218414 A1 | 9/2011 | Kamath et al. |
| 2011/0224523 A1 | 9/2011 | Budiman |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2011/0320130 A1 | 12/2011 | Valdes et al. |
| 2011/0320167 A1 | 12/2011 | Budiman |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108931 A1 | 5/2012 | Taub |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0245447 A1 | 9/2012 | Karan et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |

(56) References Cited

FOREIGN PATENT DOCUMENTS

| EP | 0127958 | 12/1984 |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2031534 | 3/2009 |
| EP | 1725163 | 12/2010 |
| WO | WO-1996/025089 | 8/1996 |
| WO | WO-1996/035370 | 11/1996 |
| WO | WO-1998/035053 | 8/1998 |
| WO | WO-1999/027849 | 6/1999 |
| WO | WO-1999/028736 | 6/1999 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO-2003/057027 | 7/2003 |
| WO | WO-2003/076893 | 9/2003 |
| WO | WO-2003/082091 | 10/2003 |
| WO | WO-2004/060455 | 7/2004 |
| WO | WO-2005/057175 | 6/2005 |
| WO | WO-2005/065538 | 7/2005 |
| WO | WO-2005/065542 | 7/2005 |
| WO | WO-2006/020212 | 2/2006 |
| WO | WO-2006/024671 | 3/2006 |
| WO | WO-2006/072035 | 7/2006 |
| WO | WO-2007/019289 | 2/2007 |
| WO | WO-2008/048452 | 4/2008 |
| WO | WO-2008/052374 | 5/2008 |
| WO | WO-2008/062099 | 5/2008 |
| WO | WO-2008/086541 | 7/2008 |
| WO | WO-2008/144445 | 11/2008 |
| WO | WO-2010/062898 | 6/2010 |
| WO | WO-2011/000528 | 1/2011 |

OTHER PUBLICATIONS

Kovatchev, B. P., et al., "Graphical and Numerical Evaluation of Continuous Glucose Sensing Time Lag", *Diabetes Technology & Therapeutics*, vol. 11, No. 3, 2009, pp. 139-143.

Steil, G. M., et al., "Closed-Loop Insulin Delivery—the Path of Physiological Glucose Control", *Advanced Drug Delivery Reviews*, vol. 56, 2004, pp. 125-144.

Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.

U.S. Appl. No. 14/077,004, Office Action dated Jul. 26, 2016.

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5. No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose

(56) References Cited

OTHER PUBLICATIONS

Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

PCT Application No. PCT/US2012/066414, International Search Report and Written Opinion of the International Searching Authority dated Feb. 22, 2013.

U.S. Appl. No. 13/683,996, Notice of Allowance dated Jan. 14, 2016.

U.S. Appl. No. 13/683,996, Office Action dated Aug. 12, 2015.

\* cited by examiner

ANALYTE MONITORING SYSTEM AND METHODS OF USE

CROSS REFERENCE TO RELATED APPLICATIONS

This application is a continuation of U.S. patent application Ser. No. 15/143,413 filed on Apr. 29, 2016, which is a continuation of U.S. patent application Ser. No. 13/683,996 filed on Nov. 21, 2012, which claims the benefit of U.S. Provisional Patent Application No. 61/563,743 filed on Nov. 25, 2011, which are expressly incorporated by reference herein in their entirety.

BACKGROUND

Analyte, e.g., glucose monitoring systems including continuous and discrete monitoring systems, generally include a small, lightweight, battery powered and microprocessor controlled system configured to detect signals proportional to the corresponding measured glucose levels using an electrometer and radio frequency (RF) signals to transmit the collected data. Certain analyte monitoring systems include a transcutaneous or subcutaneous analyte sensor configuration which is, for example, partially mounted on the skin of a subject whose analyte level is to be monitored. The sensor cell may use a two or three-electrode (work, reference, and counter electrodes) configuration driven by a controlled potential (potentiostat) analog circuit connected through a contact system.

The analyte sensor may be configured so that a portion thereof is placed under the skin of the patient so as to detect the analyte levels of the patient, with another segment of the analyte sensor adapted to be in communication with the data processing unit. The data processing unit is configured to communicate the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels.

For systems that calculate the blood glucose concentration by measuring interstitial glucose in real time, lag between the interstitial glucose and blood glucose and sensor noise can introduce error, some of which is detrimental to obtaining accurate glucose and glucose rate of change data.

It would be desirable to have a method and system to account for lag and system noise and provide robust and useful data that is relevant to the blood glucose system.

SUMMARY

The present disclosure describes embodiments including methods for overcoming sensor noise and lag between the interstitial fluid and blood, both of which can introduce error. Certain embodiments allow for a balance between signal responsiveness and the reduction in noise by a smoothing process. Certain aspects utilize a combination of algorithms, including algorithms optimized to maintain minimal expected error between the final sensor output and a corresponding reference and one that provides more stable rates of change in glucose levels. In certain aspects, lag correction algorithms designed to minimize the correlation between sensor error (with respect to reference blood glucose) and rates of change calculate glucose values with optimal point wise accuracy, and smoothing algorithms to minimize the effect of noise accurately calculate rates of change in glucose levels.

The present disclosure provides embodiments including methods for monitoring an analyte including monitoring a data stream including a set of contiguous source data points related to the analyte concentration; if a higher sample rate is desired, generating a set of monitored data streams from the set of contiguous source data points, utilizing one or more of the monitored data streams or the set of contiguous source data points to compute a maximum lag correction oriented signal, wherein the lag correction algorithm attempts to eliminate the expected error due to blood-to-interstitial glucose dynamics with reasonable but minimal regard to noise amplification, utilizing one or more of the monitored data streams or the set of contiguous source data points to generate a maximum smoothing oriented signal, wherein the smoothing algorithm attempts to eliminate noise, which includes sample time-to-sample time variation not correlated to true glucose change, utilizing the maximum lag correction oriented signal for generating analyte concentration and utilizing the maximum smoothing oriented signal for generating a rate of change in the analyte concentration.

Certain embodiments of the present disclosure include methods for monitoring an analyte including monitoring a data stream including a set of contiguous source data points related to the analyte concentration, providing a set of monitored data streams from the set of source data points, wherein each set of monitored data streams is generated utilizing a spline, up-sampling, or regularization algorithm, providing a set of maximum lag corrected signals from the set of monitored data streams, wherein each set of maximum lag corrected signals is generated utilizing correction terms based on time derivative estimates and historical monitored data stream data points that minimize the correlation between the expected glucose error and time derivative estimates or minimize the correlation between the expected glucose error and a pre-determined array of historical monitored data stream, providing a set of maximum smoothing signals from the set of monitored data streams, wherein each set of maximum smoothing signals is generated utilizing a smoothing algorithm, generating analyte concentration utilizing the maximum lag corrected signals, and generating a rate of change in the analyte concentration utilizing the maximum smoothing signals. In certain aspects, rate of change can be computed based on maximum smoothing signals using a variety of methods, including a backwards first difference approximation using the most recent two successive maximum smoothing signals measurements, Finite Impulse Response (FIR) filters employing 2 or more recent maximum smoothing signals measurements, or the slope of a Least Squares Error Fit of a line based on recent maximum smoothing signals measurements.

Certain aspects of the present disclosure include methods for monitoring an analyte including monitoring a data stream including a set of contiguous source data points related to analyte concentration, providing a set of maximum lag corrected signals from the source data points, wherein each set of maximum lag corrected signals is generated utilizing correction terms based on time derivative estimates and historical source data points that minimize the correlation between the expected glucose error and time derivative estimates or minimize the correlation between the expected glucose error and a pre-determined array of historical source data points, providing a set of maximum smoothing signals from the set of source data points, wherein each set of maximum smoothing signals is generated utilizing a smoothing algorithm, generating analyte concentration utilizing the maximum lag corrected signals, and generating a rate of change in the analyte concentration utilizing the maximum smoothing signals.

Aspects of the present disclosure include methods for monitoring an analyte including monitoring a data stream including a set of contiguous source data points related to the analyte concentration, providing a set of maximum lag corrected signals from the set of monitored data stream, wherein each set of maximum lag corrected signals is generated utilizing correction terms based on time derivative estimates and historical monitored data stream data points that minimize the correlation between the expected glucose error and time derivative estimates or minimize the correlation between the expected glucose error and a pre-determined array of historical monitored data stream, providing a set of maximum smoothing signals from the set of monitored data stream, wherein each set of maximum smoothing signals is generated utilizing a smoothing algorithm, providing a second set of maximum smoothing signals from the set of monitored data stream, wherein each of the second set of maximum smoothing signals is generated utilizing a smoothing algorithm, generating analyte concentration utilizing a weighted combination of maximum lag corrected signals and maximum smoothing signals, wherein more weight is placed on the set of maximum lag corrected signals to generate the output, and generating a rate of change in the analyte concentration utilizing a weighted combination of maximum lag corrected signals and maximum smoothing signals, where more weight is placed on the maximum smoothing signals to generate the output.

Certain aspects of the present disclosure include methods for monitoring an analyte comprising monitoring a data stream including a set of contiguous source data points related to the analyte concentration, providing a set of maximum lag corrected signals from the set of source data points, wherein each set of maximum lag corrected signals is generated utilizing correction terms based on time derivative estimates and historical source data points that minimize the correlation between the expected glucose error and time derivative estimates or minimize the correlation between the expected glucose error and a pre-determined array of historical source data points, providing a set of maximum smoothing signals from the set of source data points, wherein each set of maximum smoothing signals is generated utilizing a smoothing algorithm, generating analyte concentration utilizing a weighted combination of maximum lag corrected signals and maximum smoothing signals, where more weight is placed on the maximum lag corrected signals to generate the output and generating a rate of change in the analyte concentration utilizing a weighted combination of maximum lag corrected signals and maximum smoothing signals, where more weight is placed on the maximum smoothing signals to generate the output.

DETAILED DESCRIPTION

Figure 1:
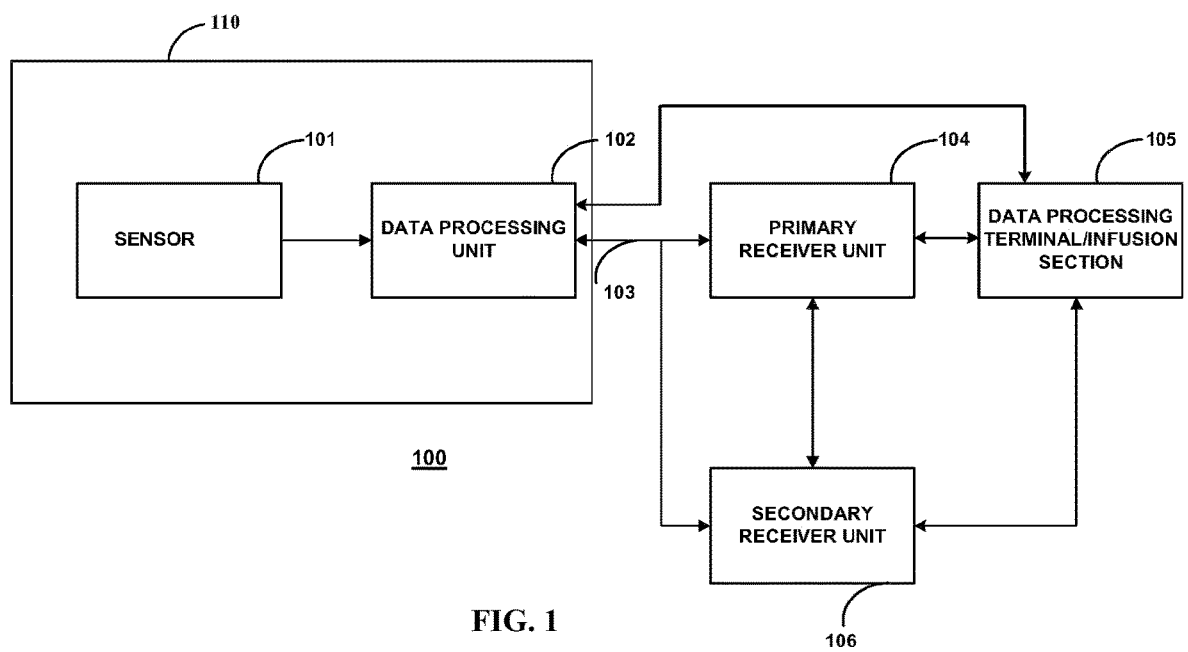
FIG. 1 shows a data monitoring and management system such as, for example, an analyte (e.g., glucose) monitoring system in accordance with certain embodiments of the present disclosure.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, exemplary methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

The present disclosure provides for the utilization of a combination of algorithms to strike a balance between responsiveness and minimizing noise. Certain embodiments involve a maximum lag correction algorithm and a maximum smoothing algorithm. The lag correcting algorithm minimizes the expected point-wise error of glucose values, resulting in accurate glucose values whereas the smoothing algorithm minimizes the sample time-to-sample time variability which provides rates of change with optimum accuracy. The development and use of lag correction algorithms can be found in U.S. Patent Publication Nos. 2010/0191085, now U.S. Pat. No. 8,224,415, 2010/0023291, now U.S. Pat. No. 8,515,517, 2009/0198118, now U.S. Pat. Nos. 8,473,022, and 7,618,369, the disclosures of each of which are incorporated herein by reference for all purposes.

In certain embodiments, algorithms compensate for lag between blood glucose (BG) and interstitial glucose (IG), measured by a sensor, by correlating time derivatives (e.g. rate estimate, acceleration estimate, band limited rate estimate, etc.) with the BG to IG discrepancy, correlating a pre-determined array of historical sensor data with the BG to IG discrepancy, and providing cancellation terms computed from the sensor signal. These algorithms can improve aggregate point wise accuracy of a continuous glucose monitoring system relative to blood glucose values. However, a consequence of the improved responsiveness is an increased susceptibility to noise due to the amplification of errors caused by noise in the time derivative calculations that are necessary to produce a rate estimate. To better estimate the rate of change, algorithms can be developed that smooth recent data to remove artifacts from noise.

In certain embodiments, lag correction algorithms selected vary in aggressiveness in order to strike a balance between levels of responsiveness and smoothing. A lag correction algorithm is deemed more aggressive when it attempts to remove the average error correlated to blood-to-interstitial glucose dynamics with less regard to the noise amplification effect it generates. A lag correction algorithm is overly aggressive if the amount of lag correction exceeds the required amount, resulting in an error of the opposite sign as compared to when no lag correction is attempted. A lag correction algorithm is deemed less aggressive if the amount of correction is somewhere between the optimal amount and no lag correction at all.

The combination of a lag correcting algorithm in combination with a smoothing algorithm can similarly be used to provide more accurate acceleration data in combination with representative glucose values.

FIG. 1 shows a data monitoring and management system such as, for example, an analyte (e.g., glucose) monitoring system in accordance with certain embodiments of the present disclosure. Embodiments of the subject disclosure are described primarily with respect to glucose monitoring devices and systems, and methods of using two or more devices in a glucose monitoring system to determine the compatibility of one or more devices in the glucose monitoring system.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

Referring to FIG. 1, the analyte monitoring system 100 includes a sensor 101, a data processing unit (e.g., sensor electronics) 102 connectable to the sensor 101, and a primary receiver unit 104 which is configured to communicate with the data processing unit 102 via a communication link 103. In aspects of the present disclosure, the sensor 101 and the data processing unit (sensor electronics) 102 may be configured as a single integrated assembly 110. In certain embodiments, the integrated sensor and sensor electronics assembly 110 may be configured as an on-body patch device. In such embodiments, the on-body patch device may be configured for, for example, RFID or RF communication with a reader device/receiver unit, and/or an insulin pump.

In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a data processing unit or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver unit 104, i.e., the secondary receiver unit 106 may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least process send data related to its configuration into a corresponding signal for transmission by the data processing unit 102.

The data processing unit 102 is coupleable to the sensor 101 so that both devices are positioned in or on the user's body, with at least a portion of the analyte sensor 101 positioned transcutaneously. The data processing unit 102 in certain embodiments may include a portion of the sensor 101 (proximal section of the sensor in electrical communication with the data processing unit 102) which is encapsulated within or on the printed circuit board of the data processing unit 102 with, for example, potting material or other protective material. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101. That is, when operating in the CGM mode, the receiver unit 104 in certain embodiments is configured to automatically receive data related to the configuration of the sensor from the analyte sensor/sensor electronics when the communication link (e.g., RF range) is maintained or opened between these components.

Referring again to FIG. 1, the data processing terminal 105 may include a personal computer, portable data processing devices or computers such as a laptop computer or a handheld device (e.g., personal digital assistants (PDAs), communication devices such as a cellular phone (e.g., a multimedia and Internet-enabled mobile phone such as an iPhone, a Blackberry device, a Palm device such as Palm Pre, Treo, or similar phone), mp3 player, pager, and the like), drug delivery device, insulin pump, each of which may be configured for data communication with the receiver via a wired or a wireless connection. Additionally, the data processing terminal 105 may further be connected to a data network (not shown).

The data processing terminal 105 may include an infusion device such as an insulin infusion pump or the like, which may be configured to administer insulin to patients, and which may be configured to communicate with the primary receiver unit 104 for receiving, among others, the measured analyte level or configuration data. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In particular embodiments, the data processing terminal 105, which may include an insulin pump, may be configured to receive the configuration signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1 may use one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

The analyte monitoring system may include an on-body patch device with a thin profile that can be worn on the arm or other locations on the body (and under clothing worn by the user or the patient), the on-body patch device including an analyte sensor and circuitry and components for operating the sensor and processing and storing signals, including configuration signals, received from the sensor as well as for communication with the reader device. For example, one aspect of the on-body patch device may include electronics to sample the voltage signal received from the analyte sensor in fluid contact with the body fluid, and to process the sampled voltage signals into the corresponding glucose values and/or store the sampled voltage signal as raw data, or to send configuration information as a signal or data.

Figure 2:
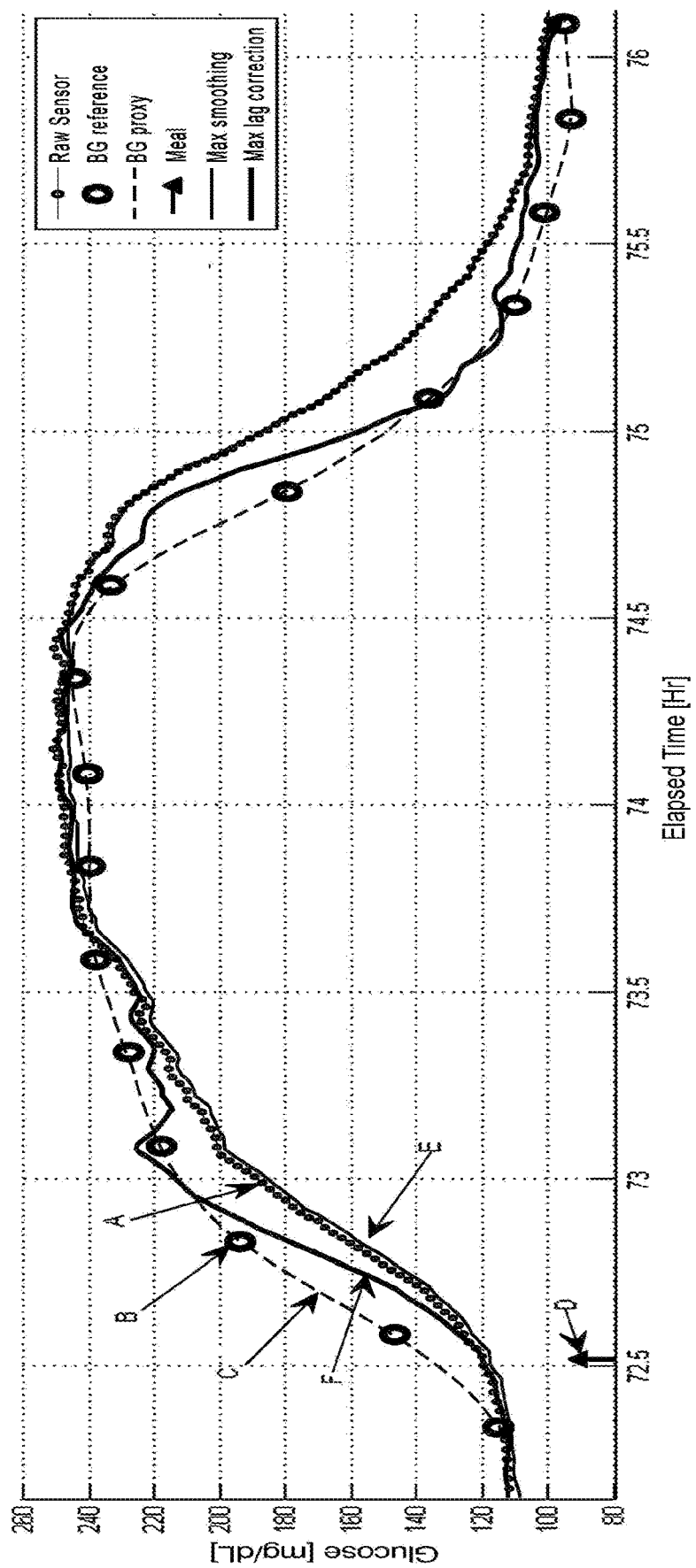
FIG. 2 illustrates data related to changes in interstitial fluid measurement and two filtered outputs as compared against discrete blood glucose measurements and an up-sampled or monitored smooth blood glucose signal.

FIG. 2 illustrates data related to changes in blood glucose levels and related data generated from an interstitial fluid measurement, such as interstitial fluid measurements taken by the analyte monitoring system of FIG. 1, processed utilizing an aggressive lag correction algorithm and a smoothing algorithm. Lag from blood glucose (BG) to interstitial glucose (IG) is illustrated in FIG. 2. The raw sensor signal measures glucose concentration in the interstitial fluid space. BG reference collected at a slower sample rate is up-sampled as BG proxy to visually match the raw sensor's sample time. Both the BG and BG proxy data are only used to provide context on some of the characteristics of IG compared to BG. Neither the BG nor BG proxy data are needed for the methods described in this invention. IG levels match BG well provided that glucose concentrations remain steady. Otherwise, IG levels are generally lower than BG while glucose increases, and higher while glucose decreases. From a point-wise perspective, this reduced responsiveness manifests itself as one source of sensor error. However, any attempt to correct for this lag results in the amplification of noise, as can be seen in the maximum lag correction line (curve F in FIG. 2). Even in the absence of lag correction, it may be necessary to process the sensor signal to filter out noise. A smoothed IG signal is shown to reduce the sample time-to-sample time fluctuations, but further increases the overall BG to IG lag, which is especially visible in curve E in FIG. 2 while glucose is increasing. The term smoothing implies the reduction of sample time-to-sample time fluctuations, but does not require the process to be limited to a retrospective operation.

Referring to FIG. 2, the first curve A represents raw sensor data. BG measurements B are up-sampled into a smooth curve C in order to visually demonstrate a more fluid progression of BG data. A meal event D is shown to increase glucose. The fifth curve E represents data processed with a smoothing curve. The sixth curve F provides output that is close to the blood glucose levels represented by curve C. Raw sensor signal is collected at a pre-determined time interval (e.g. once every 1 minute) where the signal is either: (a) pre filtered at a much faster time interval and/or processed to remove erroneous data or (b) a direct sampling from the source without any preprocessing. Blood glucose is also collected at a longer time interval (e.g. once every 15 minutes) to provide reference data. A smooth BG proxy is generated from the BG reference at a sample interval and time points that match the pre-determined time interval of the collected sensor signal. Both the BG and BG proxy data are only used to provide context, and are not needed for the methods described in this invention. A meal event initiates a rise in the patient's BG level. Maximizing the signal noise filtering is shown to produce a smoother signal at the expense of additional lag. On the other hand, maximizing lag correction allows for better point-wise agreement with BG at the expense of additional sample-to-sample variation.

Figure 3:
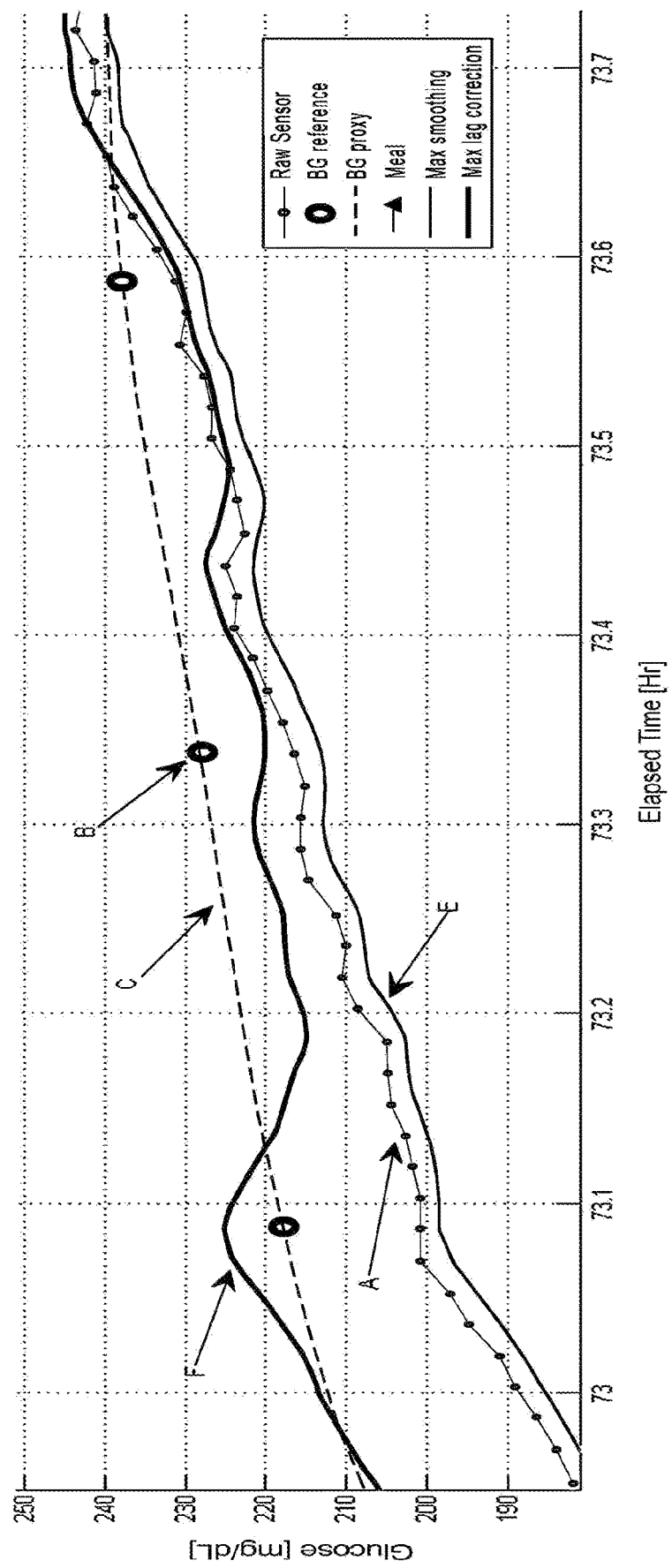
FIG. 3 illustrates a closer view of a region from FIG. 2, highlighting data during a rapid rise in glucose level illustrating how each algorithm deals with a rapid rise in glucose level.

FIG. 3 illustrates a closer view of a region (73.0 to 73.7 units of elapsed time) from FIG. 2, highlighting data during a rapid rise in glucose level illustrating how each algorithm deals with a rapid rise in glucose level. The highlighted region of FIG. 2, provided in FIG. 3, focuses on a region of rapid increase in glucose and illustrates the different way each algorithm responds. For example, during the rapid increase in glucose, curve E, generated without any lag correction, provides more accurate rate of change data because its trend matches well with that of the trend of curve C, but provides less accurate data regarding glucose concentration. In contrast, curve F generated with lag correction produces data output regarding glucose levels during the rapid increase in glucose levels that closely corresponds to curve C, representing actual blood glucose data.

Aspects of the present disclosure provide for the utilization of the combination of a lag correction algorithm and a smoothing algorithm in a continuous glucose monitoring system to optimize the accuracy of readings related to glucose levels and the rates of change in glucose levels. The achievement of better accuracy for readings of both glucose level and its rate of change is important in first understanding the real changes in blood glucose and properly managing its level.

Figure 4:
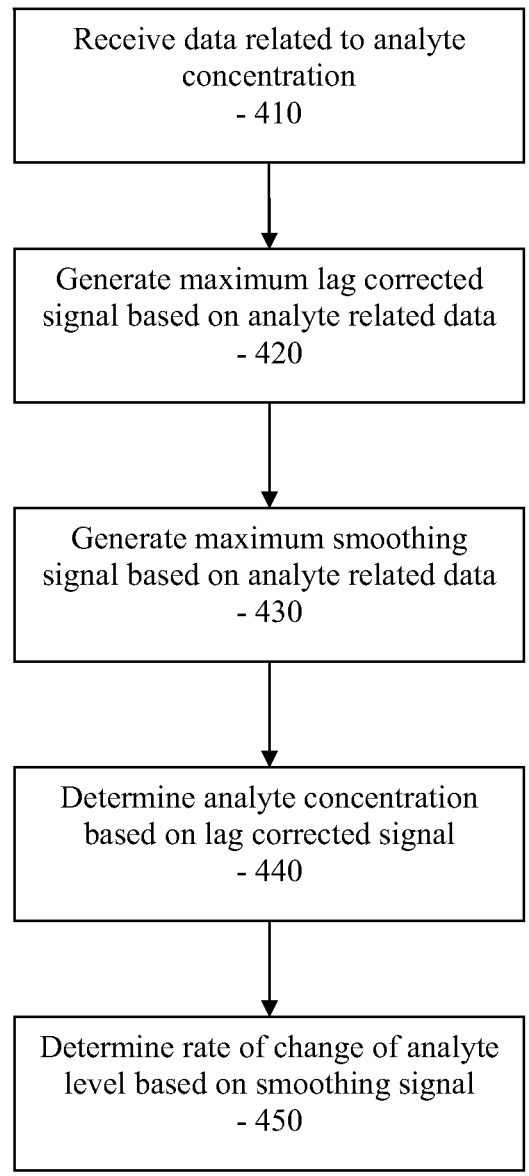
FIG. 4 is a flow chart illustrating certain embodiments for monitoring and processing analyte data.

FIG. 4 is a flow chart illustrating certain embodiments for monitoring and processing analyte data. Referring to FIG. 4, a processing unit, such as data processing unit 102 or receiver unit 104 of the analyte monitoring system 100 of FIG. 1, receives data related to an analyte concentration (410), which may be received from a sensor, such as sensor 101 of analyte monitoring system 100 of FIG. 1. The received data is analyzed and a maximum lag corrected signal is generated (420). In certain embodiments, the maximum lag corrected signal is generated by utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points. In certain embodiments, the maximum lag correction signal is generated by utilizing an aggressive lag correction algorithm configured to drive one or more of the correlation between the expected glucose error and the time derivative estimates or the correlation between the expected glucose error and a pre-determined array of historical data points, to zero. The maximum lag corrected signal is analyzed to determine a corrected analyte concentration (440).

Referring still to FIG. 4, the received data is also analyzed and a maximum smoothing signal is generated (430) by applying a smoothing algorithm to the received data and the maximum smoothing signal is analyzed to determine the rate of change of the monitored analyte level (450).

Figure 5:
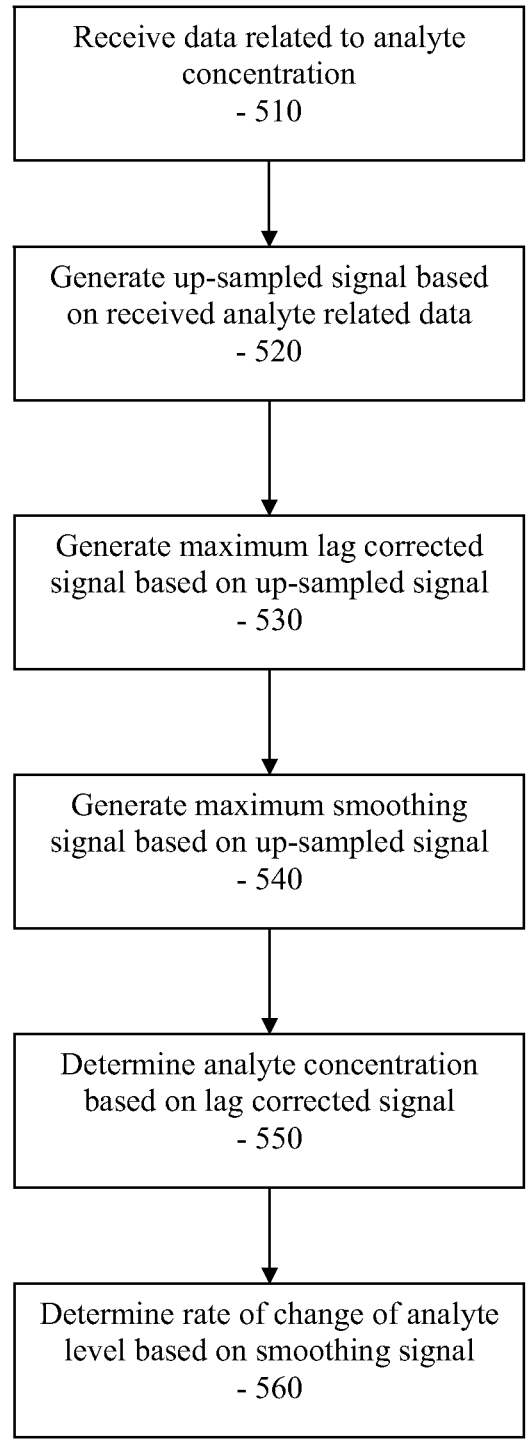
FIG. 5 is a flow chart illustrating certain embodiments for monitoring and processing analyte data utilizing monitored data stream.

FIG. 5 is a flow chart illustrating certain embodiments for monitoring and processing analyte data utilizing monitored data stream. Referring to FIG. 5, a processing unit, such as data processing unit 102 or receiver unit 104 of the analyte monitoring system 100 of FIG. 1, receives data related to an analyte concentration (510), which may be received from a sensor, such as sensor 101 of analyte monitoring system 100 of FIG. 1. The received data is sampled at a high speed to generate a monitored data stream (520). In certain embodiments, the monitored data stream is optionally generated utilizing a spline, up-sampling, or regularization algorithm. The monitored data stream is analyzed and a maximum lag corrected signal is generated (530). In certain embodiments, the maximum lag corrected signal is generated by utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points. In certain embodiments, the maximum lag correction signal is generated by utilizing an aggressive lag correction algorithm configured to drive one or more of the correlation between the expected glucose error and the time derivative estimates or the correlation between the expected glucose error and a pre-determined array of historical data points, to zero. The maximum lag corrected signal is analyzed to determine a corrected analyte concentration (550).

Referring still to FIG. 5, the received data is also analyzed and a maximum smoothing signal is generated (540) by applying a smoothing algorithm to the received data and the maximum smoothing signal is analyzed to determine the rate of change of the monitored analyte level (560).

Figure 6:
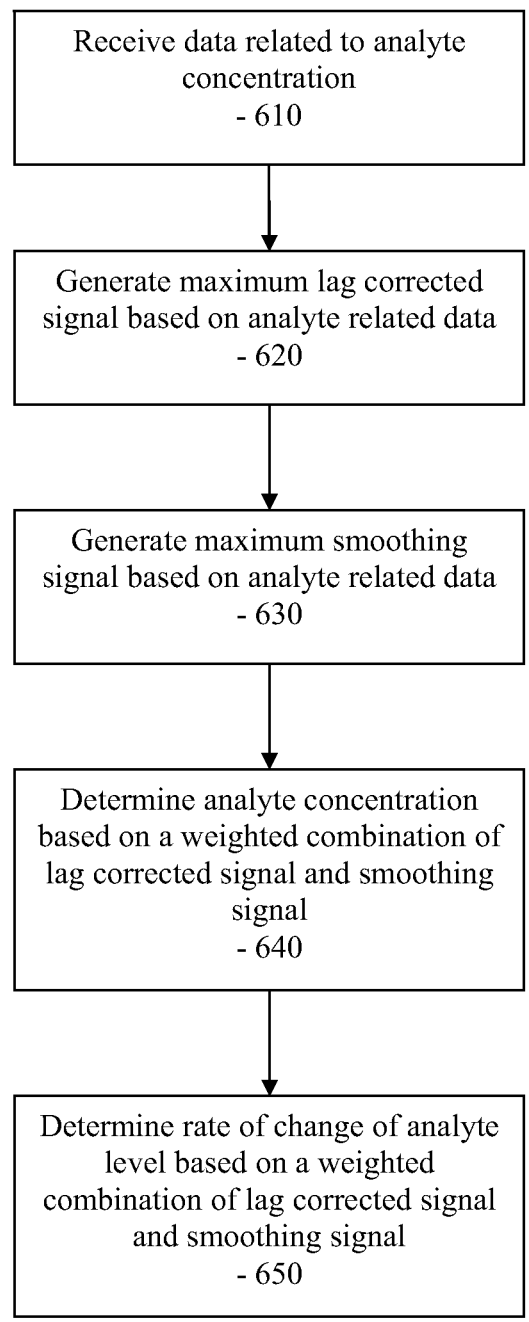
FIG. 6 is a flow chart illustrating certain embodiments for monitoring and processing analyte data utilizing weighted data processing.

FIG. 6 is a flow chart illustrating certain embodiments for monitoring and processing analyte data utilizing weighted data processing. Referring to FIG. 6, a processing unit, such as data processing unit 102 or receiver unit 104 of the analyte monitoring system 100 of FIG. 1, receives data related to an analyte concentration (610), which may be received from a sensor, such as sensor 101 of analyte monitoring system 100 of FIG. 1. The received data is analyzed and a maximum lag corrected signal is generated (620). In certain embodiments, the maximum lag corrected signal is generated by utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points. In certain embodiments, the maximum lag correction signal is generated by utilizing an aggressive lag correction algorithm configured to drive one or more of the correlation between the expected glucose error and the time derivative estimates or the correlation between the expected glucose error and a pre-determined array of historical data points, to zero.

Referring still to FIG. 6, the received data is also analyzed and a maximum smoothing signal is generated (630) by applying a smoothing algorithm to the received data. After determination of the maximum lag corrected signal and the maximum smoothing signal, both signals are analyzed and weighted to determine the analyte concentration (640) and rate of change of the monitored analyte level (650). In certain embodiments, the analyte concentration determination is made by weighting the maximum lag corrected signal more heavily than the maximum smoothing signal and the rate of change determination is made by weighting the maximum smoothing signal more heavily than the maximum lag corrected signal.

In certain embodiments, there is provided a method for monitoring an analyte comprising monitoring a data stream including a set of contiguous source data points related to the concentration of an analyte, providing one or more sets of maximum lag corrected signals from the one or more sets of monitored data stream, wherein each set of maximum lag corrected signals is generated utilizing correction terms based on time derivative estimates and historical monitored data stream data points, and wherein parameters for the maximum lag correction minimize the correlation between the expected glucose error and time derivative estimates and minimize the correlation between the expected glucose error and a pre-determined array of historical monitored data stream, providing one or more sets of maximum smoothing signals from the set of monitored data stream, wherein each set of maximum smoothing signals is generated utilizing a smoothing algorithm, determining analyte concentration utilizing the one or more sets of maximum lag corrected signals, and determining a rate of change in the analyte concentration utilizing the one or more sets of maximum smoothing signals.

In certain aspects, providing the one or more sets of maximum lag corrected signals includes utilizing an aggressive lag correction algorithm, the lag correction algorithm configured to drive one or more of the correlation between the expected glucose error and the time derivative estimates or the correlation between the expected glucose error and a pre-determined array of historical data points, to zero.

In certain aspects, monitoring a data stream including a set of contiguous source data points related to the analyte concentration includes monitoring a data stream received from a transcutaneously positioned analyte sensor, where the transcutaneously positioned analyte sensor in certain embodiments is operatively coupled to a continuous glucose monitoring system.

In certain embodiments, one or more sets of maximum smoothing signals are further utilized to determine acceleration data of the analyte concentration.

In accordance with another embodiment, there is provided a method for monitoring an analyte comprising monitoring a data stream including a set of contiguous source data points related to analyte concentration, providing one or more sets of maximum lag corrected signals from the set of contiguous source data points, wherein each set of maximum lag corrected signals is generated utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points, providing one or more sets of maximum smoothing signals from the set of contiguous source data points, wherein each set of maximum smoothing signals is generated utilizing a smoothing algorithm, determining analyte concentration utilizing the one or more sets of maximum lag corrected signals, and determining a rate of change in the analyte concentration utilizing the one or more sets of maximum smoothing signals.

In accordance with another embodiment of the present disclosure, there is provided a method for monitoring an analyte comprising monitoring a data stream including a set of contiguous source data points related to analyte concentration, providing one or more sets of maximum lag corrected signals from the set of contiguous source data points, wherein each set of maximum lag corrected signals is generated utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points, providing one or more sets of maximum smoothing signals from the set of contiguous source data points, wherein each set of maximum smoothing signals is generated utilizing a smoothing algorithm, determining analyte concentration utilizing a weighted combination of the one or more sets of maximum lag corrected signals and the one or more sets of maximum smoothing signals, wherein more weight is placed on the one or more sets of maximum lag corrected signals to determine the analyte concentration, and determining a rate of change in the analyte concentration utilizing a weighted combination of the one or more sets of maximum lag corrected signals and the one or more sets of maximum smoothing signals, where more weight is placed on the one or more sets of maximum smoothing signals to determine the rate of change.

In accordance with still another embodiment, there is provided a method for monitoring an analyte comprising monitoring a data stream including a set of contiguous source data points related to analyte concentration, providing one or more sets of maximum lag corrected signals from the set of contiguous source data points, wherein each set of maximum lag corrected signals is generated utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points, providing a first one or more sets of maximum smoothing signals from the set of contiguous source data points, wherein each set of maximum smoothing signals is generated utilizing a smoothing algorithm, providing a second one or more sets of maximum smoothing signals from the set of contiguous source data points, wherein each of the second set of maximum smoothing signals is generated utilizing a second smoothing algorithm, determining analyte concentration utilizing a weighted combination of the one or more sets of maximum lag corrected signals and the first and second one or more sets of maximum smoothing signals, wherein more weight is placed on the one or more sets of maximum lag corrected signals to determine the analyte concentration, and determining a rate of change in the analyte concentration utilizing a weighted combination of the one or more sets of maximum lag corrected signals and the first and second one or more sets of maximum smoothing signals, where more weight is placed on the first and second one or more sets of maximum smoothing signals to determine the rate of change.

In certain embodiments, the first smoothing algorithm and the second smoothing algorithm are different.

In certain embodiments, the method further includes averaging the first one or more sets of maximum smoothing signals and the second one or more sets of maximum smoothing signals.

An apparatus in accordance with another embodiment includes one or more processors, and a memory storing instructions which, when executed by the one or more processors, causes the one or more processors to monitor a data stream including a set of contiguous source data points related to the concentration of an analyte, to provide one or more sets of monitored data stream from the set of contiguous source data points, wherein each set of monitored data stream is generated utilizing a spline, up-sampling, or regularization algorithm, to provide one or more sets of maximum lag corrected signals from the one or more sets of monitored data stream, wherein each set of maximum lag corrected signals is generated utilizing correction terms based on time derivative estimates and historical monitored data stream data points, and wherein parameters for the maximum lag correction minimize the correlation between the expected glucose error and time derivative estimates and minimize the correlation between the expected glucose error and a pre-determined array of historical monitored data stream, to provide one or more sets of maximum smoothing signals from the set of monitored data stream, wherein each set of maximum smoothing signals is generated utilizing a smoothing algorithm, to determine analyte concentration utilizing the one or more sets of maximum lag corrected signals and to determine a rate of change in the analyte concentration utilizing the one or more sets of maximum smoothing signals.

In certain embodiments, the instructions to provide the one or more sets of maximum lag corrected signals include instructions to utilize an aggressive lag correction algorithm, the lag correction algorithm configured to drive one or more of the correlation between the expected glucose error and the time derivative estimates or the correlation between the expected glucose error and a pre-determined array of historical data points, to zero.

In certain embodiments, the instructions to monitor the data stream including the set of contiguous source data points related to the analyte concentration includes instructions to monitor a data stream received from a transcutaneously positioned analyte sensor operatively coupled to the one or more processors.

In certain embodiments, the one or more sets of maximum smoothing signals are further utilized to determine acceleration data of the analyte concentration.

An apparatus in accordance with another embodiment includes one or more processors, and a memory storing instructions which, when executed by the one or more processors, causes the one or more processors to monitor a data stream including a set of contiguous source data points related to analyte concentration, to provide one or more sets of maximum lag corrected signals from the set of contiguous source data points, wherein each set of maximum lag corrected signals is generated utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points, to provide one or more sets of maximum smoothing signals from the set of contiguous source data points, wherein each set of maximum smoothing signals is generated utilizing a smoothing algorithm, to determine analyte concentration utilizing the one or more sets of maximum lag corrected signals and to determine a rate of change in the analyte concentration utilizing the one or more sets of maximum smoothing signals.

An apparatus in accordance with still another embodiment includes one or more processors, and a memory storing instructions which, when executed by the one or more processors, causes the one or more processors to monitor a data stream including a set of contiguous source data points related to analyte concentration, to providing one or more sets of maximum lag corrected signals from the set of contiguous source data points, wherein each set of maximum lag corrected signals is generated utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points, to provide one or more sets of maximum smoothing signals from the set of contiguous source data points, wherein each set of maximum smoothing signals is generated utilizing a smoothing algorithm, to determine analyte concentration utilizing a weighted combination of the one or more sets of maximum lag corrected signals and the one or more sets of maximum smoothing signals, wherein more weight is placed on the one or more sets of maximum lag corrected signals to determine the analyte concentration and to determine a rate of change in the analyte concentration utilizing a weighted combination of the one or more sets of maximum lag corrected signals and the one or more sets of maximum smoothing signals, where more weight is placed on the one or more sets of maximum smoothing signals to determine the rate of change.

An apparatus in accordance with still yet another embodiment includes one or more processors, and a memory storing instructions which, when executed by the one or more processors, causes the one or more processors to monitor a data stream including a set of contiguous source data points related to analyte concentration, to provide one or more sets of maximum lag corrected signals from the set of contiguous source data points, wherein each set of maximum lag corrected signals is generated utilizing correction terms based on time derivative estimates and historical source data points, and wherein parameters for the maximum lag correction minimize the correlation between the expected glucose error and time derivative estimates and minimize the correlation between the expected glucose error and a pre-determined array of historical source data points, to provide a first one or more sets of maximum smoothing signals from the set of contiguous source data points, wherein each set of maximum smoothing signals is generated utilizing a smoothing algorithm, to provide a second one or more sets of maximum smoothing signals from the set of contiguous source data points, wherein each of the second set of maximum smoothing signals is generated utilizing a second smoothing algorithm, to determine analyte concentration utilizing a weighted combination of the one or more sets of maximum lag corrected signals and the first and second one or more sets of maximum smoothing signals, wherein more weight is placed on the one or more sets of maximum lag corrected signals to determine the analyte concentration and to determine a rate of change in the analyte concentration utilizing a weighted combination of the one or more sets of maximum lag corrected signals and the first and second one or more sets of maximum smoothing signals, where more weight is placed on the first and second one or more sets of maximum smoothing signals to determine the rate of change.

In certain embodiments, the first smoothing algorithm and the second smoothing algorithm are different.

Certain embodiment includes instructions to average the first one or more sets of maximum smoothing signals and the second one or more sets of maximum smoothing signals.

Various other algorithms and analysis may be applied in certain embodiments to the monitored analyte signal received from sensor 101 of analyte monitoring system 100 (FIG. 1) to correct for lag and noise. Further, the weight of lag corrected and smoothed signals are varied in embodiments in order to effectively maximize noise cancellation and system accuracy.

The present disclosure contemplates modifications as would occur to those skilled in the art. For example, it is contemplated that a variety of the lag correction algorithms and the smoothing algorithms disclosed herein can be developed, altered or otherwise changed utilizing the principles provided in the present disclosure, as would occur to those skilled in the art without departing from the spirit of the present disclosure. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present disclosure and is not intended to make the scope of the present disclosure dependent upon such theory, proof, or finding. While the disclosure has been illustrated and described in detail in the figures and foregoing description, the same is considered to be illustrative and not restrictive in character, it being understood that only certain embodiments have been shown and described and that all changes and modifications that come within the spirit of the disclosure are desired to be protected.

What is claimed is:

1. An analyte monitoring system, comprising:
an analyte sensor configured to have at least a portion disposed in interstitial fluid of a user and generate a plurality of data points related to a concentration of an analyte in the interstitial fluid;
a data processing device operatively coupled to the analyte sensor, wherein the data processing device is configured to:
generate one or more first data points by applying one or more lag correction algorithms to the plurality of data points, wherein the one or more first data points are used to generate an output related to the analyte concentration from the plurality of data points related to the analyte concentration;
generate one or more second data points by applying one or more smoothing algorithms to the plurality of data points, wherein the second data points are used to generate the output related to the analyte concentration from the plurality of data points related to the analyte concentration;
determine the analyte concentration based on a first weighted combination, wherein the first weighted combination comprises the one or more first data points and the one or more second data points with more weight placed on the one or more first data points than the one or more second data points; and
determine, using the data processing device of the analyte monitoring sensor, a rate of change in the analyte concentration based on a second weighted combination, wherein the second weighted combination comprises the one or more first data points and the one or more second data points with more weight placed on the one or more second data points than the one or more first data points; and
a data processing terminal having a memory configured to receive the determined analyte concentration, the data processing terminal comprising a drug delivery device configured to administer therapy based on the determined analyte concentration.

2. The analyte monitoring system of claim 1, wherein the data processing device is further configured to generate one or more third data points from the plurality of data points related to the analyte concentration.

3. The analyte monitoring system of claim 2, wherein the first weighted combination comprises the one or more first data points, the one or more second data points, and the one or more third data points with more weight placed on the one or more first data points than the one or more second data points and the one or more third data points.

4. The analyte monitoring system of claim 3, wherein generating the one or more third data points from the plurality of data points related to the analyte concentration of the analyte comprises applying a third algorithm to the plurality of data points related to the analyte concentration.

5. The analyte monitoring system of claim 4, wherein the third algorithm is a smoothing algorithm.

6. The analyte monitoring system of claim 1, wherein the data processing device is further configured to determine an average of the one or more first data points and the one or more second data points.

7. The analyte monitoring system of claim 1, wherein the data processing device comprises sensor electronics coupled to the analyte sensor and is configured to receive the plurality of data points related to the analyte concentration.

8. The analyte monitoring system of claim 1, wherein the analyte sensor includes a plurality of electrodes including a working electrode comprising an analyte-responsive enzyme.

9. The analyte monitoring system of claim 8, wherein the enzyme is bound to a polymer disposed on the working electrode.

10. The analyte monitoring system of claim 8, wherein the working electrode comprises a mediator.

11. The analyte monitoring system of claim 10, wherein the mediator is bound to a polymer disposed on the working electrode.

12. The analyte monitoring system of claim 10, wherein the mediator is crosslinked with a polymer disposed on the working electrode.

13. The analyte monitoring system of claim 1, wherein the analyte sensor includes a plurality of electrodes including a working electrode comprising a mediator.

14. The analyte monitoring system of claim 13, wherein the mediator is bound to a polymer disposed on the working electrode, or wherein the mediator is crosslinked with the polymer disposed on the working electrode.

15. The analyte monitoring system of claim 1, wherein the data processing terminal comprises a smartphone.

16. The analyte monitoring system of claim 1, wherein the drug delivery device comprises an insulin infusion device.

17. The analyte monitoring system of claim 1, further comprising a receiver unit configured to receive the determined analyte concentration, wherein the receiver unit is one or both of a wrist watch and an arm band.

* * * * *